United States Patent [19]

Caroli

[11] 4,275,749
[45] Jun. 30, 1981

[54] ELECTRICALLY DRIVEN CONTINUOUS TOOTH BRUSH

[76] Inventor: Celso Caroli, Via Sardegna, 16, Savignano sul Panaro (Modena), Italy

[21] Appl. No.: 38,842

[22] Filed: May 14, 1979

[30] Foreign Application Priority Data

Jun. 5, 1978 [IT] Italy .............................. 40086 A/78

[51] Int. Cl.³ .......................................... A45D 24/00
[52] U.S. Cl. ..................................... 132/11 A; 15/23
[58] Field of Search ..................... 132/11 A, 11 R, 85, 132/9, 73.6, 76.4; 128/52, 393, 357; 15/23–29, 38, 22 A, 32–34, 37

[56] References Cited

U.S. PATENT DOCUMENTS

| | | | |
|---|---|---|---|
| 2,017,881 | 10/1935 | Wiseman | 132/73.6 UX |
| 2,829,655 | 4/1958 | Bau | 132/84 R |
| 3,126,021 | 3/1964 | May | 132/76.4 |
| 3,216,034 | 11/1965 | Johnson | 15/23 |
| 3,278,963 | 10/1966 | Bond | 132/11 R |
| 3,373,739 | 3/1968 | Rankin | 132/11 R |
| 3,459,199 | 8/1969 | Connell | 132/11 R |

FOREIGN PATENT DOCUMENTS 572585 1/1958 Italy .......................................... 132/85

Primary Examiner—G. E. McNeill
Attorney, Agent, or Firm—Browdy and Neimark

[57] ABSTRACT

Electrically driven continuous tooth brush, characterized by the fact that it consists of an interchangeable brush of cylindrical shape, the rotation of which is driven by an electric motor having a reversable sense of rotation, contained in a handgrip type housing. The brush body is peripherally screened from the mucous membrane of the mouth by a protective cap of cylindrical surface section shape with approximately 180° angular width.

8 Claims, 13 Drawing Figures

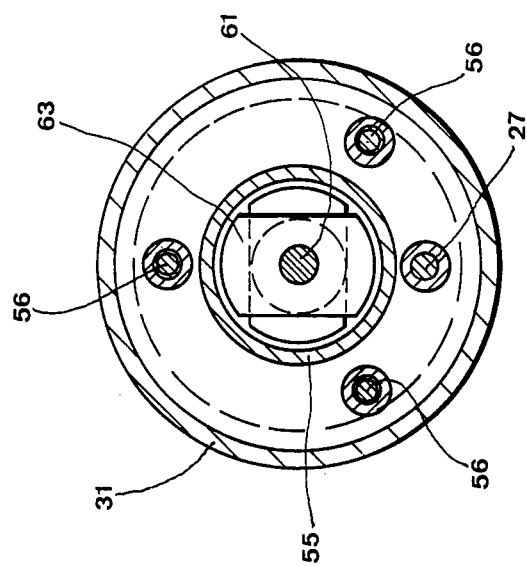
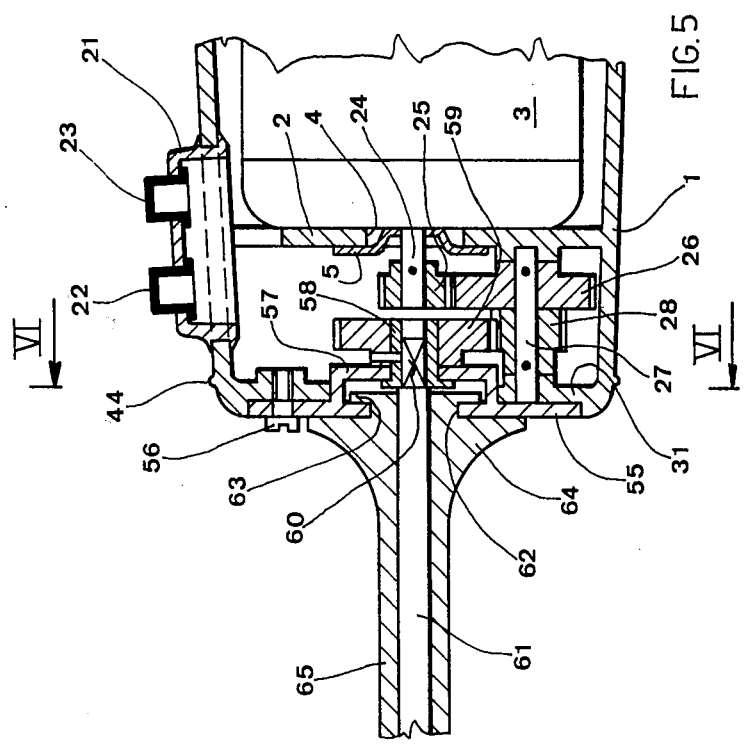

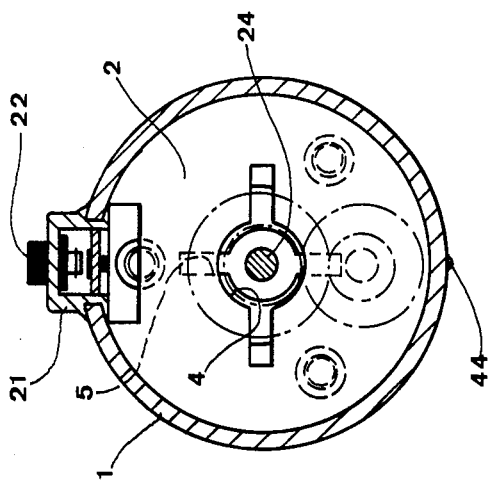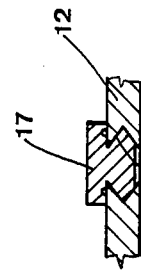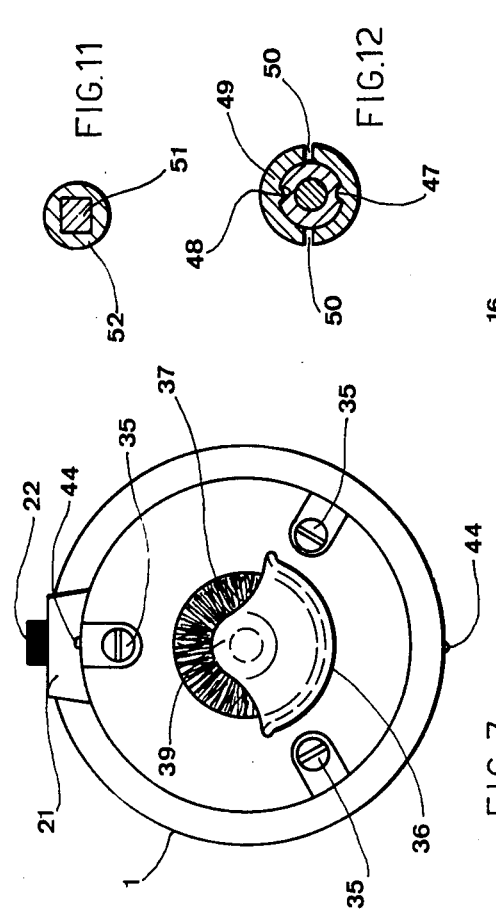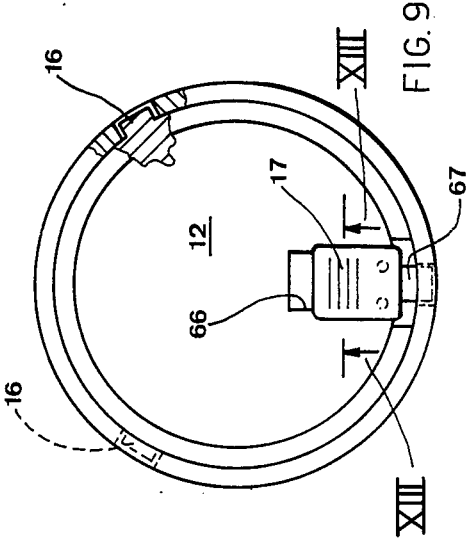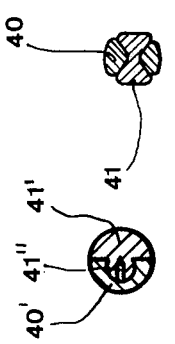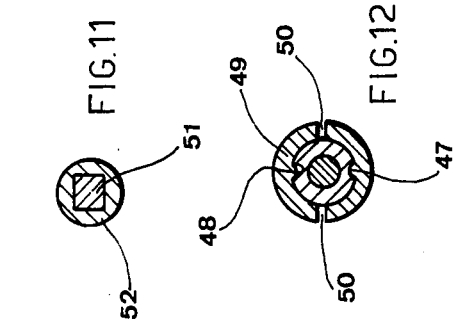

ELECTRICALLY DRIVEN CONTINUOUS TOOTH BRUSH

This invention concerns an electrically driven continuous tooth brush, that is to say, an instrument equipped with a non-traditional tooth brush, automatically driven with continuous motion, that is, neither alternative nor straight-line nor angularly oscillating motion. The state of art, prior to this invention, is characterized by electric tooth brushes of alternative motion within a rather limited rotation sector, driven by an electric motor housed in the cover forming the handle, the output shaft of which drives with angular oscillating motion, directly or by means of a gear, a transverse arm keyed to a pivot, at the outer end of which an interchangeable brush with traditional manual type tooth brush bristles arranged in alined groups is fixed. This prior state of art presents some defects and inconveniences, deriving from the fact that thus driven tooth brushes f. i. tend to extract the impurities from the intertooth connections during the go stroke of an angular oscillation, whereas they tend to push them back into them during the return stroke, and viceversa, thus determining an incomplete cleaning; moreover, the oscillating motion of considerable frequency accompanied by an intense vibration of the tooth brush body, due to the pounding of the inversion shocks at the end of each stroke, has a damaging effect on the gums, which are strained by dry blows from the bristles and therefore start to separate from the teeth with inflammatory complications; moreover, the inversions of the angular motion determine the rapid expulsion of the toothpaste from the initial moment of the cleaning operation in such a way that the operator is compelled to renew its dabbing various times in order to complete the cleaning operation; finally, the tooth brushes of traditional instruments have to be very small because of the oscillating motion, practically, at the very best, of the dimensions of so-called manual children's tooth brushes, compelling therefore the grownup operator not only to dab a very small quantity of toothpaste on his brush compared to his own necessity, but also to extend the cleaning operation with loss of time. From these defects and inconveniences derives the necessity of resolving the new technical problem of finding an electrically driven tooth brush, which does not only consent to receive a sufficient quantity of toothpaste so that the operator is not compelled to dab it on more than once in the course of one operation, but also permits to avoid blows and vibration at the gums, extracting at the same time with certainty the impurities and food rests in general from the intertooth connections without any harmful effect on the gums, performing, on the contrary, an efficient massage of the latter; all this improving the manual action, which is still considered the best and most efficient, in spite of the appearance of the automatic oscillating tooth brush. This invention resolves in a principal manner completely the above said new technical problem by means of the adoption of a cylindrical tooth brush driven in continuous rotation with inversion of the rotation during the passage from one dental arch to the other, during the passage from one branch to the other and during the passage from the outer to the inner part of the set of teeth; said tooth brush being sideways equipped with a sector cap for the protection of the inner mucous cheek membrane; the inner surface of this cap can be at a distance or tangent or interfering with the extremities of the bristles; means being mainly foreseen: to fix the tooth brush at the end of the instrument stem in an interchangeable way without removing the cap; to keep the whole of tooth brush and cap protected, when the instrument is not used.

Some realizations of the invention are illustrated, purely as an indication, in the four schematic design tables here enclosed, in which:

FIG. 5 is a cut-away view of a blown-up detail of the front part of the instrument intended to show the quick coupling of the stem-brush-cap group;

FIG. 6 is a section VI—VI of FIG. 5;

FIG. 7 is a left side view of FIG. 2;

FIG. 8 is the section VIII—VIII of FIG. 1;

FIG. 9 is a partially cut-away right side view of FIG. 2;

Figures 1, 2:
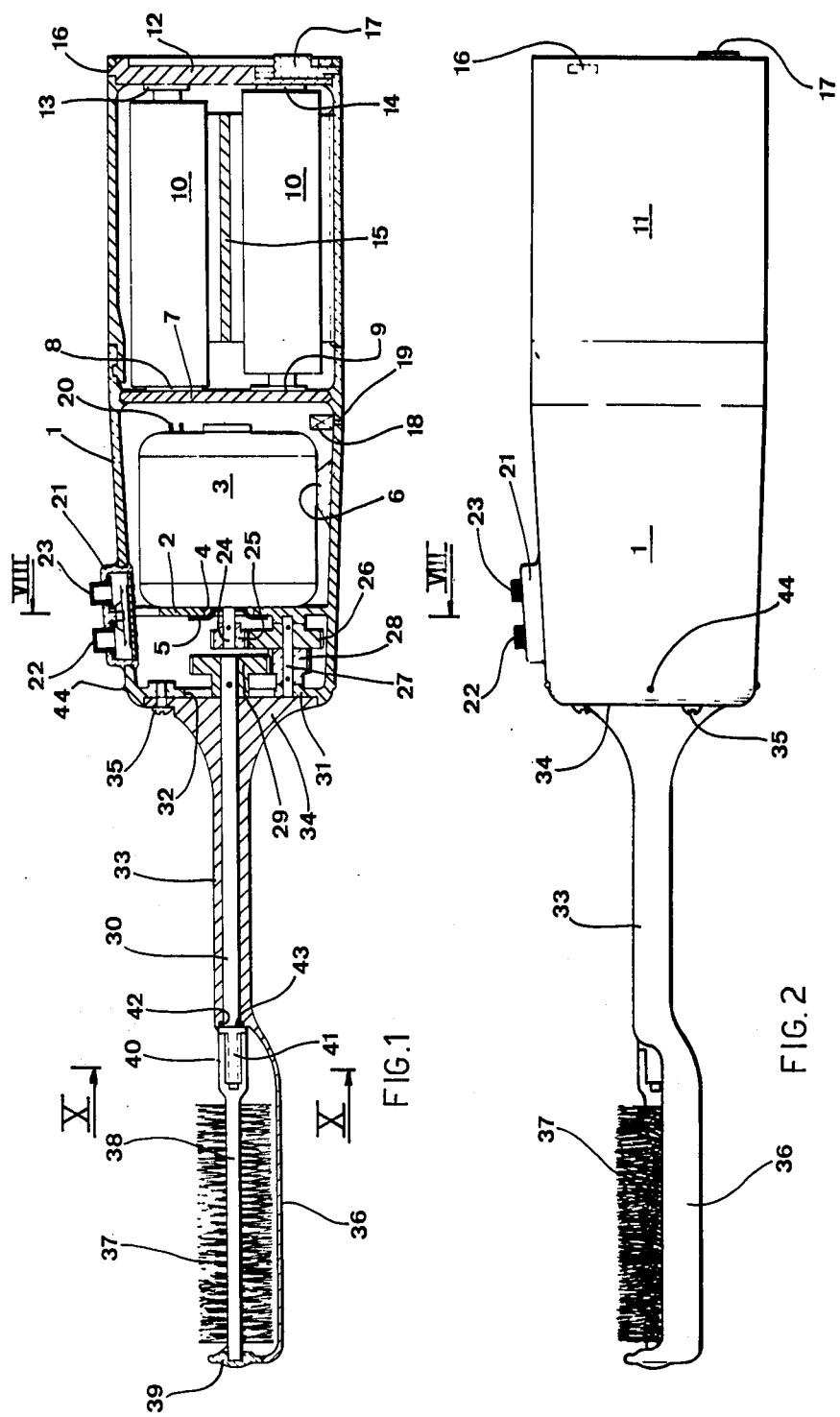
FIG. 1 is a longitudinal section of the instrument.
FIG. 2 is a side view of the instrument.
Figure 3:
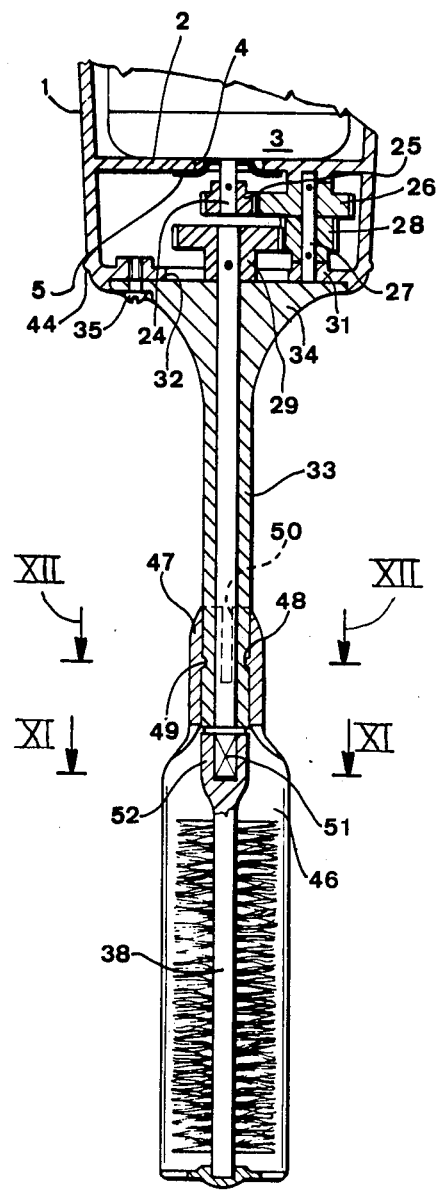
FIG. 3 is a blown-up and interrupted sectional view of the front part of the instrument intended to show the quick coupling of the tooth brush-cap group.

FIGS. 10 and 10' are cut-away views like X—X of FIG. 1, illustrating two couplings between shaft and brush;

FIG. 11 is the section XI—XI of FIG. 3 intended to show a type of coupling of the brush to the shaft;

FIG. 12 is the section XII—XII of FIG. 3 intended to show the coupling of the cap to the stem;

FIG. 13 is the section XIII—XIII of FIG. 9 intended to shown the fixing of the glass bottom cover, being part of the instrument housing.

Figure 4:
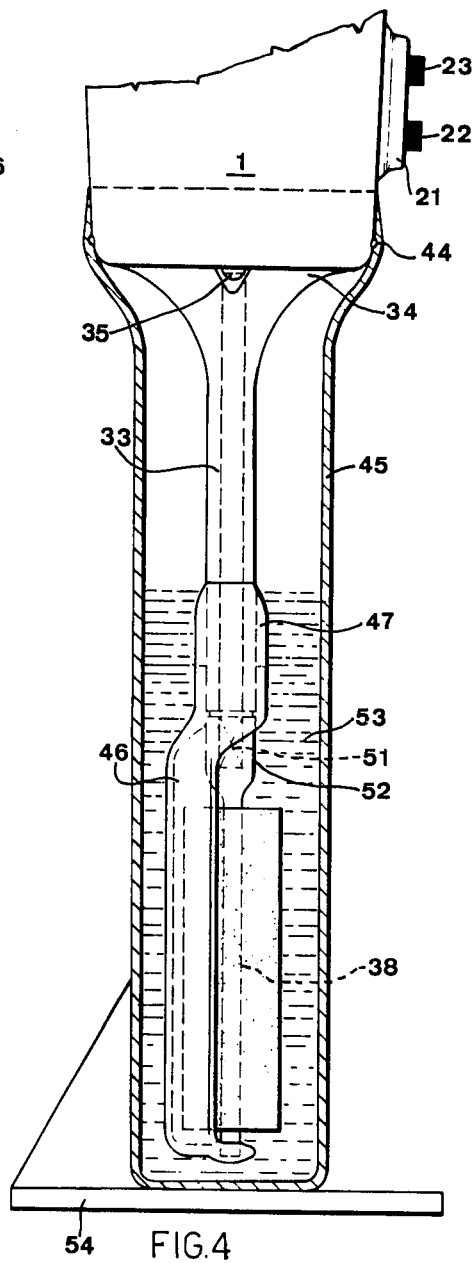
FIG. 4 is a blown-up and interrupted view of the instrument intended to show a possible protection of the tooth brush with corresponding vertical support.

With reference to those figures, the indications are as follows: 1 is the central instrument housing body equipped with the electric motor 3 support diaphragm 2 fixed to the diaphragm 2 slot 4 by means of spreaded elastic sectors 5; 6 indicates the inner motor 3 centering projections of the body 1; 7 indicates a body 1 diaphragm supporting the electric contacts 8 and 9 of the accumulators or piles 10 contained in the glass with the body 11 and bottom cover 12 bearing the contacts 13 and 14; 15 indicates inner electric feed element 10 centering tongues of the body 11; 16 is a peripheral projection couple of cover 12 inserted in corresponding slits of the body 11; 17 is a radially sliding latch penetrating into an analog cover 12 fixing slit of the body 11; 18 indicates an electric connection intended to receive through the bore 19 of the body 1 a possible accumulator 10 recharge plug; 20 indicates the connections for the motor 3 main, not represented; 21 is a box element fixed into a slit of the housing 1 intended to support the push buttons 22 and 23, which control the two rotation senses of the motor 3 shaft 24, on which the pinion 25, meshing with the gear wheel 26, is keyed; the latter is keyed to the intermediate shaft 27, on which the gear wheel 28, meshing with the final gear wheel 29 fixed to the shaft 30 is keyed; the shaft 27 being in a rotating way supported by the diaphragm 2 and by the front diaphragm 31, equipped with the bore 32; 33 is a rotating support coupling of shaft 30 equipped with a flange 34 to be attached to the diaphragm 31 with the screws 35; 36 indicates a cap, screening the oral cavity mucous membrane and the lips from the contact with the cylindrical tooth brush 37, the stem of which is supported by the end 39 of cap 36 and, moreover, anti-rotationwise, fixed into the male tang 41 of the shaft 30 end with its female tang 40; the outer surfaces of the tangs 40 and 41 being able to rest on a cylindrical surface in order to avoid blunt projections; 40' and 41' are tang elements corresponding to 40 and 41; 41" is a split of 41, 42 a retainer ring to avoid water entry between 30 and 33; 43 is a striking surface; 44 indicates peripheral projections of the front part of housing 1 intended to receive the protection container element 45 (FIG. 4); 46 (FIG. 3) indicates a cap like 36, moreover equipped with a fixing end 47, having an undercut 48 to be inserted in a groove 49 of the coupling 33 and diametrically opposed splits in order to facilitate the insertion; 51 is a prismatic male tang for the insertion of the stem 38 in the female tang 52; 53 indicates an antiseptic fluid in the container 45; 54 is a pedestal forming one single body with 45; 55 (FIG. 5) is the flange to be mounted by means of screws 56 to the diaphragm 31 of the support 57 centered in the diaphragm 31 bore 32; 58 indicates a bush inserted in and supported by the center bore of the support 57 to consent the gear wheel 59 to be keyed to it just like 29; at the inside of this bush being keyed the shaft 61 end 60 just like 30; 62 indicates a slot in the flange 55 serving for the introduction of the crosspiece of the restrained joint flange 64 end of the coupling 65 just like 33; 66 (FIG. 9) is a guide cavity of the sliding latch 17 obturator 67 made in the cover 12.

The instrument is operated in the following way: once spreaded the toothpaste on the bristles 37 (FIG. 1), the whole 36, 37, 38, 39 and possibly 40, 41 is introduced into the mouth, then the push button 22 or 23 is pressed in order to obtain the rotation sense suitable to clean the upper arch of teeth from the bottom to the top, internally and externally, thus obtaining a convenient action for the extraction of the impurities from the intertooth connections, expelling them with sureness and thus avoiding to push them into the connections or under the gums, effecting at the same time a beneficial massage of the gums without the damaging transverse component; during the cleaning operation the cap 36, which cannot rotate, remaining adherent to the inner mucous membrane of the cheek in order to protect it from the bristles. Practically, the execution details, the dimensions, the materials, and the shape of the invention can, at any rate, vary without causing the latter to leave its juridical dominion, infact, the thus conceived invention is liable to modifications and variations, all entering into the limits of the inventive concept. Thus, f. i., the speed reduction unit 24-25-26-27-28-29 might be replaced by another reduction type or might even be lacking: and this also depending on the motor 3 characteristics; moreover, the push buttons 22 and 23 might be differently situated or also reduced to one only, possibly of the sliding type; thus, also the piles 10 might be replaced by rechargeable accumulators and/or be housed in a separate container connected by cable with the housing 1, in that case of smaller dimensions: and the motor 3 might even be fed by the electric power net with suitable insertions of voltage convertors and reductions to obtain the proper safety values; thus, also the joints of the various elements might be carried out in a different manner and the caps like 36 and 46, too, might be adherent or even interfering slightly with the peripheral path of the bristles 37 in such a manner that the tooth brush as well as the caps become self-cleaning. The tooth brush according to the invention being suitable for interchangeability of the stem 33 supporting the brush 37-38 shaft for insertion of different qualities of cylindrical brushes with bristles as well as for interchangeability with brushes equipped with rubber tentacles such as those at present placed like a cap on the finger tips in order to make a pronounced gum massage; moreover, the type of electric switch or the corresponding push buttons 22, 23 or contacts in general might be changed. However to observe that the term of "tooth brush" is prevalently used to indicate the whole instrument and that the part intended for the tooth cleaning should more properly be called "tooth brush body". As to the joint of the tooth brush handle with female tang equipped with longitudinal elements 40 tapered towards the inside at the shaft end with male tang equipped with longitudinal elements at a right angle with 40, it can be noted that, besides the stability, it presents a particular elasticity and graduality of the coupling in axial as well as in transversal sense; the coupling being of the "eight shape" elastically forced type; as to the tooth brush handle with female tang 40' at the shaft end with male tang 41', it can be noted that a similar joint is particularly stable because of the transversal right angle introduction with a release made possible by the slit 41" in the projection of the male, having a cylindrical contour for more than 180° and, therefore, presenting an undercut compared to the female cavity being cylindrical as well with corresponding cylindrical contour of more than 180°, the coupling thus being of "C" type shape. As to the width of the angular cap 36 sector, this can normally reach values near 180° or even of 180° and can possibly exceed them. Finally, all the elements may be replaced by technically equivalent elements.

I claim:

1. An electric, continuously driven tooth brush comprising a handle to be grasped by a user; a hollow stem extending from said handle; a reversible electric motor housed in said handle; a rotatable shaft connected to said electric motor to be rotated thereby extending axially through said stem, said shaft having an end extending beyond said stem; an interchangeable cylindrical brush body; means for removably fixing said brush body to said end of said shaft; a protective cap for the mucous membrane and tissues of the mouth, said cap extending over said cylindrical brush body along it length and over substantially a 180° arc; and means for supporting the tooth brush when not in use with said cap and said brush body in a antiseptical solution.

2. An electric tooth brush according to claim 1, including means for reversing the rotational direction of said motor to provide movement of the bristles from a users gums toward the extremity of the users teeth for each arch within the users mouth.

3. An electric tooth brush according to claim 1, wherein said means for removably fixing said brush body to said end of said shaft comprise a female tang consisting of two longitudinal opposed bodies tapered towards their inside on one of said brush body and said end, and wherein the other of these members is equipped with a corresponding male tang of a profile with eight-shape neck suitable for insertion in a resilient and forced 90° coupling between the two said female tang bodies.

4. An electric tooth brush according to claim 1, wherein said means for fixing said brush body to said shaft comprise on an end of said brush body a female tang having a cavity with a C shape contour for a more than 180° sector, and wherein said shaft is equipped with a male tang, having a radial corresponding projection which can be inserted by force into said cavity, said projection being equipped with a notch along a center line.

5. An electric tooth brush according to claim 1, wherein said means for supporting the tooth brush with said brush body and said cap in an antiseptic solution includes a container, equipped with a base in order to be kept in a stable vertical position, said container at its upper part having a cylindrical mouth to receive the front end of said handle containing said electric motor, said mouth presenting in its initial part an inner diameter corresponding to that of said end of said handle and, extending therefrom, an axial locking tapering, the depth of said container beneath said tapering being longer than the length of said cap and said brush body so as to assure these can be completely covered by the antiseptic solution.

6. An electric tooth brush according to claim 1, wherein said cap forms a single body with said stem, which supports said shaft at said handle in a rotating manner, and including a tang coupling said shaft to said brush body, said tang projecting inside said cap, and forming an extension above an end of said stem.

7. An electric tooth brush according to claim 1, wherein said cap is equipped with an end joint with longitudinal slits for forced insertion in an end of said stem supporting said shaft for rotation, said joint being internally equipped with a ring projection for snap release fixing in a groove in an outer surface of said stem.

8. An electric, continuously driven tooth brush comprising a handle to be grasped by a user; a hollow stem extending from said handle; a reversible electric motor housed in said handle; a rotatable shaft connected to said electric motor to be rotated thereby extending axially through said stem, said shaft having an end extending beyond said stem; an interchangeable cylindrical brush body; means for removably fixing said brush body to said end of said shaft; and a protective cap for protecting the mucous membrane and tissues of the mouth, said cap extending over said cylindrical brush body along its length and over substantially a 180° arc.

* * * * *